US00PP13260P2

(12) United States Plant Patent
Kent

(10) Patent No.: US PP13,260 P2
(45) Date of Patent: Nov. 19, 2002

(54) AECHMEA PLANT NAMED '228'

(76) Inventor: Jeffrey C. Kent, 510 4th St. 2A, Encinitas, CA (US) 92024

( * ) Notice: Subject to any disclaimer, the term of this patent is extended or adjusted under 35 U.S.C. 154(b) by 75 days.

(21) Appl. No.: 09/761,929

(22) Filed: Jan. 17, 2001

(51) Int. Cl.[7] ..... A01H 5/00

(52) U.S. Cl. ..... Plt./370

(58) Field of Search ..... Plt./370

*Primary Examiner*—Kent L. Bell

(57) ABSTRACT

A new cultivar of Aechmea named '228' characterized by its compactness and its foliage that is variegated as contrasted to the dark forest green coloration of *Acehmea fascieta* 'Morgana' of which it is a sport.

1 Drawing Sheet

BOTANICAL CLASSIFICATION

*Aechmea fasciata.*

VARIETY DENOMINATION

'228'.

BACKGROUND OF THE INVENTION

The present invention relates to a newly developed inter-specific hybrid *Aechmea fasciata* resulting from a planned breeding program that I conduct on an ongoing basis. The objects of the breeding program include the crossing of selected parent plants from the numerous, compatible species within the genus, to obtain plants with novel and attractive phenotypes, coloration, and flowering forms. Other important selection factors may include ultimate plant size and shape, disease resistance, tolerance to different soil and growing conditions and vigor.

Among the objects of my program are to produce plants of the Bromeliaceae family which will be attractive to the consumer; which will develop reasonably rapidly under controlled conditions, and which retain for a long term, highly attractive and bright inflorescence; i.e., bract coloration, after being induced into the flowering stage. It is a specific object to provide a low maintenance plant which will be a long term decorative appointment offering an exotic color splash in the home of a buyer, or serve as a substitute for flowering plants which have a shorter flowering duration in, for example, indoor plant and flower scapes. Finally, it is an object to develop plants which may be easily and efficiently multiplied by state-of-the-art tissue culture methods while continuing the distinctive characteristics of the plants through progressive clonal generations.

The instant plant is a naturally occurring whole plant sport of an *Aechmea fasciata* 'Morgana' (unpatented). It was discovered as a single plant growing in a cultivated planting of 'Morgana'. With the recognition that this sport satisfied the objects of the breeding program, the individual was isolated and set aside for further observation and testing. The resulting selection has been assigned the designation '228' for purposes of identification. This plant has been reproduced by division at Vista, Calif., and the plants resulting have been determined to be identical to the original selection in all distinguishing characteristics. The superior attributes of this plant will be revealed in the botanical description to follow.

SUMMARY OF THE INVENTION

The attributes of the plant '228' which distinguish it from the its parent *Aechmea fascieta* 'Morgana' are as follows This sport shows variegated foliage having a medium light green coloration in the middle of the leaves and a creamy white margin. This contrasts dramatically from the solid forest green coloration of the foliage of the parent. This variegation provides a large contrast to the coloration of the flower.

BRIEF DESCRIPTION OF THE DRAWING

The single color photograph depicts a mature specimen of the plant in mid to late flowering stage. Illustrated are the mature leaves, scape bracts, primary bracts and floral bracts. The color definitions in the specification have been taken from The R.H.S. Colour Chart of The Royal Horticultural Society. The colors depicted are believed to be of a high level of color fidelity and are believed to be as close to the actual coloration of the plant as possible in a photographic illustration of this quality. However, due to factors such as light reflectance, cultural conditions and horticultural practices, the coloration of this plant should be understood to be approximate. For example, the bract color might slightly fade if the plant is subjected to bright light and the leaf color may vary depending on the composition and the concentration of fertilizer which may be applied to the plant.

BOTANICAL DESCRIPTION OF THE PLANT

Age when described: 4–6 weeks.
Parentage: *Aechmea fasciata* 'Morgana'.

PROPAGATION

Method of Asexual Reproduction: Division.
Where reproduction took place: Kents Bromeliads Nursery Vista, Calif.
Plant:
- *Type.*—Monocot perennial.
- *General characteristics.*—Medium in size Overall height from soil surface including inflorescence — 15"–18". Overall spread — 18"–22".
- *Habit.*—Spreading Tender at temperatures below 40° F.

Leaves:
- *Number.*—13–18.
- *Size.*—Large. Length 10"–15". Width: 2.5–4".

*Shape*.—Oval pointed.
*Attitude*.—Upper leaves — ascending. Lower leaves — declinate.
*Texture*.—Velvety upper and under sides.
*Ribs & veins*.—Ordinary.
*Margin*.—Single serrations, sharp and deep.
*Coloration*.—RHS 4D along margins adaxial and abaxial; 143A in middle adaxial and abaxial.
*Petiole*.—None.

Scape bracts:
*Shape*.—Acute lanceolate serrated.
*Size*.—1¾ to 2½" long by ½ to ¾" wide.
*Margins*.—Prickled and serrated; lightly white wooly.
*Texture*.—Tomentose.
*Color*.—56A abaxial and adaxial.

Primary bracts:
*Shape*.—Acute lanceolate serrated.
*Size*.—2 to 2¾" long by ¾ to 1" wide.
*Margins*.—Prickled and serrated; lightly white wooly tomentose.
*Color*.—56A abaxial and adaxial.

Floral bracts:
*Shape*.—Acute lanceolate serrated.
*Size*.—1¼ to 1½" long by ½ to ¾" wide.
*Margins*.—Prickled and serrated; lightly white wooly tomentose.
*Color*—56A abaxial and adaxial.

Bud:
*Size*.—Small, 1" by ¼".
*Form*.—Cylindrical.
*Color*.—When sepals first divide — 61C. When petals begin to unfold — 97A. When at anthesis. Inside petals — 82D. Reverse of petals — 82-C.
*Sepals*.—Number — 3. Shape — lanceolate; apex — acute. Size — ¾" long by ¼" wide. Color abaxial — 62A. adaxial — 58D.
*Calyx*.—Shape — pear. Diameter — ¾". Aspect — glandular. Odor when rubbed — none.
*Peduncle*.—Length — ⅛". Aspect — smooth. Strength — erect. Color — 2D.

Flower:
*Blooming habit*.—Location where observations were made: Coastal southern California. Date: Mid July. Time of Day: Approximately noontime. Blooms once at any time of year upon application of gas.
*Other habit*.—In mature plant, full color is reached in 14 weeks after induction at any time of year.

Inflorescence: Average size when fully expanded 6 to 7" wide, 10" tall.
*Borne*.—Singly.
*Stems*.—Sessile.
*Form*.—When first open: tubular; retains its form to the end.
*Petalage*.—Single row. Number of petals under normal conditions: 3.
*Color*.—Center of flower: 76B. Base of petals adaxial and abaxial: 76D. Adaxial: 61C to 97A to 82D. Abaxial: 61C to 97A to 82C.

Petals:
*Texture*.—Soft. Unaffected by wet or hot weather.
*Appearance*.—Inside: Shiny. Outside: Shiny. Form — Oval.
*Arrangement*.—Imbricate. No petaloids in center.
*Persistence*.—Drop off cleanly.
*Fragrance*. —None.
*Lastingness*.—On plant: short, 5–9 days from initial emergence to flower; color changes from 61C to 97A to final color of 82C to 82D. Flower dries on plant in 2–3 days. As cut flower — 14 days or more, if the cut flower is in a cut grouping of scape, primary and floral bracts.

Reproductive organs:
*Androecium*.—Stamens: Anthers: Size — Small, ⅛"–¼". Number — 6. Color — 4D. Arrangement — Regular around styles. Filaments: Threads: medium, ¾"–1". Color — 56D to translucent. Pollen: Color — 1C. Quantity — sparse.
*Gynoecium*.—Pistil: one per flower. Styles: Columnar. Length — medium ¾ to 1"; thin. Stigmas: Color 138B to translucent. Ovaries — superior.

Fruit:
*Variety*.—Fertile.
*Form*.—Oblong.
*Aspect*.—Glandular.
*Color* (*mature*).—200B.
*Sepals*.—Caducous.

Susceptibility to pests and disease: None observed to date.

What is claimed is:

1. A new and distinct variety of Aechmea plant named '228', as illustrated and described herein.

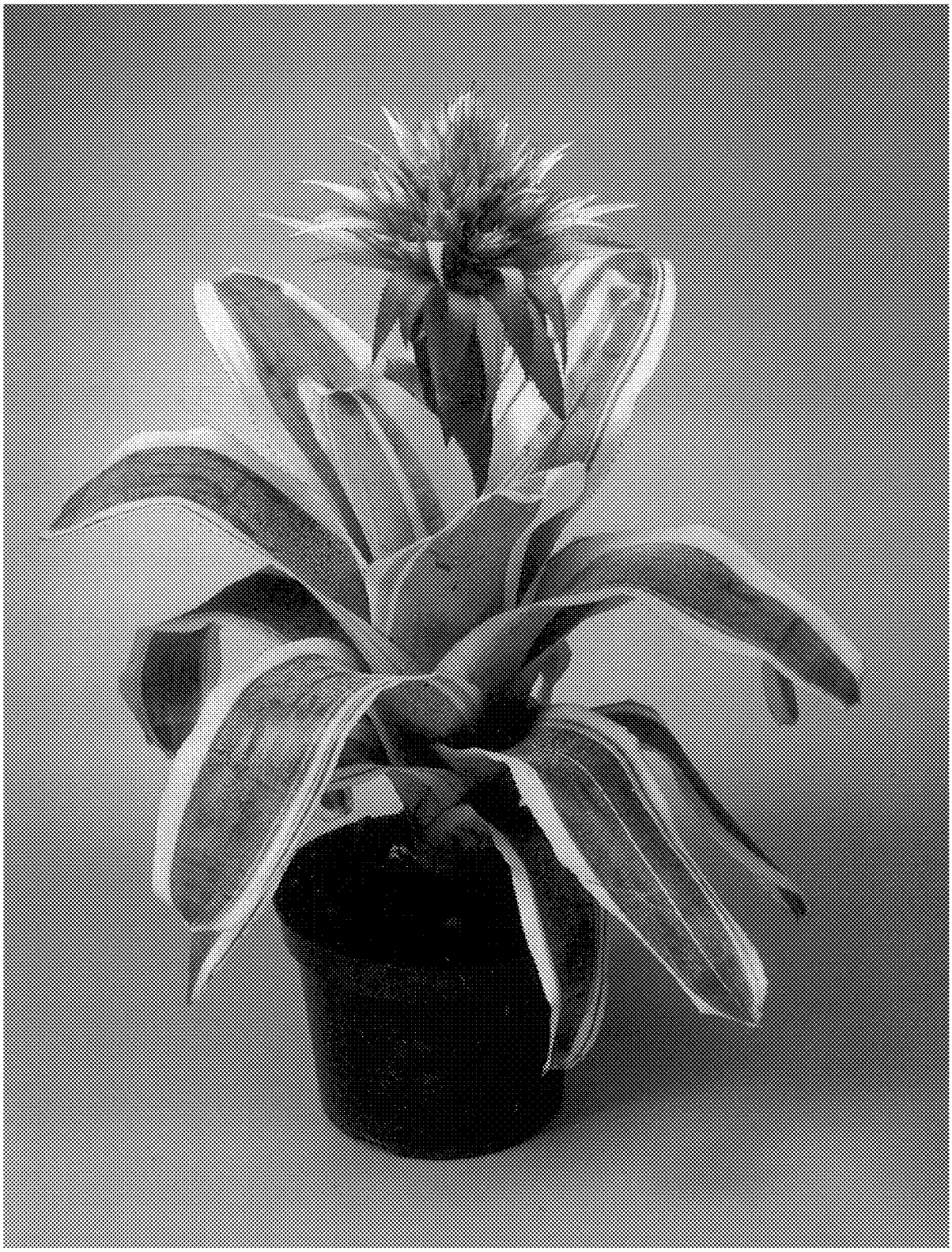

* * * * *